(12) United States Patent
Khorasani

(10) Patent No.: US 7,929,743 B2
(45) Date of Patent: Apr. 19, 2011

(54) DISPLAYING BREAST TOMOSYNTHESIS COMPUTER-AIDED DETECTION RESULTS

(75) Inventor: George Allen Khorasani, Sunnyvale, CA (US)

(73) Assignee: Hologic, Inc., Marlborough, MA (US)

( * ) Notice: Subject to any disclaimer, the term of this patent is extended or adjusted under 35 U.S.C. 154(b) by 868 days.

(21) Appl. No.: 11/906,566

(22) Filed: Oct. 2, 2007

(65) Prior Publication Data

US 2009/0087067 A1    Apr. 2, 2009

(51) Int. Cl.
  *G06K 9/00*    (2006.01)
  *A61B 6/04*    (2006.01)
(52) U.S. Cl. .......................... 382/128; 382/274; 378/37
(58) Field of Classification Search .................. 382/100, 382/128, 129, 130, 131, 132, 133, 134, 157, 382/168, 181, 199, 203, 214, 232, 254, 260, 382/274, 276, 286, 287, 291, 298, 305, 309, 382/312; 715/700; 345/419, 619; 378/21, 378/37

See application file for complete search history.

(56) References Cited

U.S. PATENT DOCUMENTS

| | | | | |
|---|---|---|---|---|
| 6,023,275 | A * | 2/2000 | Horvitz et al. | 715/700 |
| 6,628,815 | B2 * | 9/2003 | Wang | 382/132 |
| 6,630,937 | B2 * | 10/2003 | Kallergi et al. | 345/619 |
| 7,072,501 | B2 * | 7/2006 | Wood et al. | 382/132 |
| 7,245,754 | B2 * | 7/2007 | Goto | |
| 7,630,533 | B2 * | 12/2009 | Ruth et al. | 382/131 |
| 7,783,089 | B2 * | 8/2010 | Kaufhold et al. | 382/128 |
| 2003/0212327 | A1 | 11/2003 | Wang | |
| 2005/0113681 | A1 | 5/2005 | Defreitas et al. | |
| 2005/0285853 | A1 * | 12/2005 | Morita et al. | 345/419 |
| 2005/0289472 | A1 * | 12/2005 | Morita et al. | |

(Continued)

FOREIGN PATENT DOCUMENTS

WO    WO02/43801    6/2002

(Continued)

OTHER PUBLICATIONS

Takacs, et al. "Fast Detection of Mammographic Masses with Difficult Case Exclusion" IEEE Workshop on intelligent Data Acquisition and Advanced Computing Systems p. 424-428.

(Continued)

*Primary Examiner* — Seyed Azarian
(74) *Attorney, Agent, or Firm* — Brian J. Daiuto

(57) ABSTRACT

Methods, systems, and related computer program products for processing and displaying computer-aided detection (CAD) results in conjunction with breast x-ray tomosynthesis data are described. For one preferred embodiment, as a user pages through a notional stack of tomosynthesis reconstructed slice images (Tr images), including a detection-containing Tr image on which a CAD marker is to be displayed at an identified coordinate location, one or more CAD proximity markers is displayed at that coordinate location on one or more neighboring Tr images. While not themselves indicative of CAD findings on their respective Tr images, the CAD proximity markers encourage user attention toward the coordinate location of the CAD detection marker of the detection-containing Tr image. Preferably, the CAD proximity markers are of noticeably different size from each other and from the CAD detection marker to promote their perception in the peripheral vision of the user during the paging process.

20 Claims, 8 Drawing Sheets

U.S. PATENT DOCUMENTS

| | | | |
|---|---|---|---|
| 2006/0093199 | A1 | 5/2006 | Fram et al. |
| 2006/0100507 | A1* | 5/2006 | Mertelmeier |
| 2006/0215888 | A1* | 9/2006 | Habets et al. |
| 2007/0003119 | A1* | 1/2007 | Roehrig et al. |
| 2007/0122021 | A1* | 5/2007 | Zingaretti et al. |
| 2008/0155468 | A1 | 6/2008 | Rosander et al. |

FOREIGN PATENT DOCUMENTS

| | | | |
|---|---|---|---|
| WO | WO2006/055830 A2 * | 5/2006 | |

OTHER PUBLICATIONS

International Preliminary Report on Patentability and Written Opinion from related PCT Application No. PCT/US2008/078080 dated Apr. 15, 2010.

International Search Report from related PCT Application No. PCT/US2008/078080 dated Aug. 27, 2009.

* cited by examiner

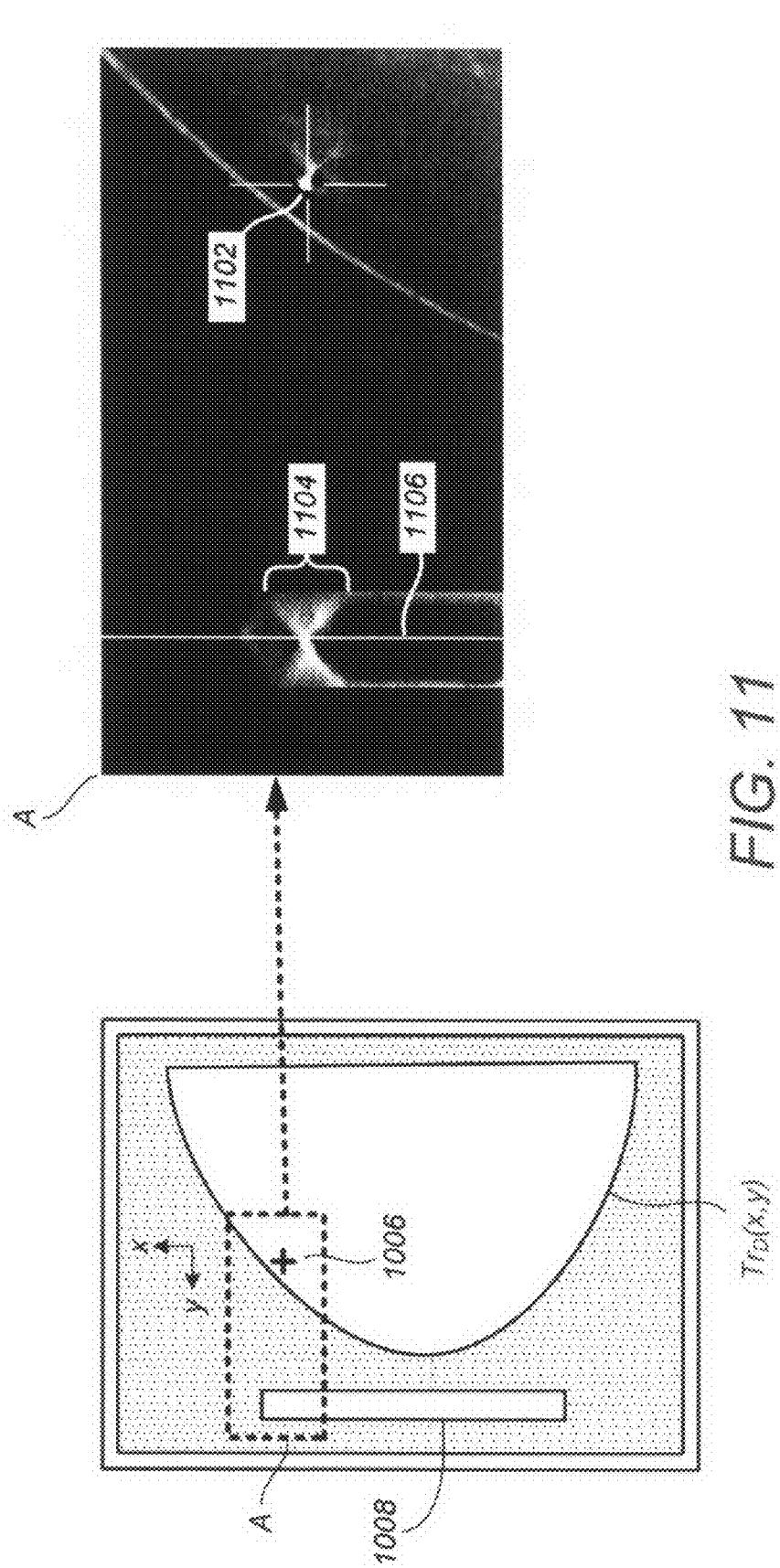

DISPLAYING BREAST TOMOSYNTHESIS COMPUTER-AIDED DETECTION RESULTS

FIELD

This patent specification relates to the computer-aided detection of abnormalities in medical images. More particularly, this patent specification relates to the display of computer-aided detection results for breast tomosynthesis data volumes.

BACKGROUND AND SUMMARY OF THE DISCLOSURE

Progress toward all-digital medical imaging environments has substantially increased the speed at which large amounts of medical image information can be accessed and displayed to a radiologist. As used herein, radiologist generically refers to a medical professional that analyzes medical images and makes clinical determinations therefrom, it being understood that such person might be titled differently, or might have differing qualifications, depending on the country or locality of their particular medical environment. X-ray based imaging for breast cancer screening/diagnosis is a particularly important field that is experiencing such information-expanding technological progress.

In what is referenced herein as conventional x-ray mammography, a stationary x-ray source projects x-rays through a breast that is immobilized by compression against a breast platform, while a stationary x-ray detector on the opposite side of the breast platform captures the x-rays to form a projection x-ray image. In the United States, two views are typically taken of each breast, including a craniocaudal (CC) view, in which the breast platform is horizontal and the x-rays are projected in a head-to-toe direction, and a mediolateral oblique (MLO) view, in which the breast platform is tilted at an angle (usually about 45 degrees) and the x-rays are projected normal to the breast platform from an inner-upper direction toward a lower-outer direction. For each patient in this typical scenario, the radiologist then carefully examines four images (left CC, left MLO, right CC, right MLO) to detect what are often subtle abnormalities indicative of a cancerous condition, such as particular types of microcalcification clusters and spiculated densities.

Although conventional x-ray mammography is still one of the best methods for detecting early forms of breast cancer, and is the modality approved by the U.S. Food and Drug Administration (FDA) to screen for breast cancer in women who do not show symptoms of breast disease, it is still possible for cancers to be missed by the radiologist reviewing the conventional x-ray mammograms. For example, for breasts that are high in dense fibroglandular content as compared to fat content, which is common for younger and/or smaller-breasted patients, conventional x-ray mammograms often contain saturated bright areas that can obscure cancerous conditions.

For these and other reasons, substantial attention and technological development has been dedicated toward breast x-ray tomosynthesis, which is similar in many respects to conventional x-ray mammography except that, for any particular view such as the CC or MLO view, the x-ray source is no longer stationary, but instead rotates through a limited angle relative to the breast platform normal (e.g., −15 degrees to +15 degrees) while several projection images (e.g., 10-15 projection images) are acquired by the x-ray detector. The several projection images are then mathematically processed to yield a relatively high number (e.g., 40-60) of tomosynthesis reconstructed images, each corresponding to a different slice of breast tissue, which can then be examined by the radiologist. Whereas a particular cancerous lesion positioned within a region of dense fibroglandular tissue might have been obscured in a single conventional x-ray mammogram view, that lesion could be readily apparent within a set of tomosynthesis reconstructed images representative of individual slices through the dense fibroglandular tissue. Examples of breast x-ray tomosynthesis systems can be found in U.S. Pat. No. 5,872,828, U.S. Pat. No. 7,123,684, and U.S. Pat. No. 7,245,694, each of which is incorporated by reference herein.

In additional to dedicated breast tomosynthesis systems, at least one proposal has been made for a combined-modality system capable of both conventional x-ray mammogram and breast x-ray tomosynthesis capabilities. The parent company of the assignee of this patent specification, Hologic, Inc., of Bedford, Mass., has demonstrated at trade shows in this country a fused, multimode mammography/tomosynthesis system that takes either or both of conventional x-ray mammograms and tomosynthesis projection images, either in single or multiple compressions/immobilizations of the breast. With regard to x-ray radiation dosage concerns, progress continues toward lowering per-projection image dosage such that the total radiation dose per breast is comparable to that of a conventional x-ray mammogram, while still maintaining good signal-to-noise ratio in the tomosynthesis projection and/or tomosynthesis reconstructed images.

Computer-aided detection (CAD) refers to the use of computers to analyze medical images to detect anatomical abnormalities therein, and/or the use of computers to otherwise process image information in a manner that facilitates perception of the medical image information by a radiologist. Sometimes used interchangeably with the term computer-aided detection are the terms computer-aided diagnosis, computer-assisted diagnosis, or computer-assisted detection. In an abnormality detection context, a CAD algorithm usually identifies a preliminary set of candidate detections in a medical image and then selects which ones, if any, will qualify as actual CAD detections based on a variety of computed features associated with the candidate detections. The CAD results, i.e., the body of information associated with the operation of the CAD algorithm on the medical image, are most often communicated in the form of annotation maps comprising graphical annotations (CAD markers) overlaid on a diagnostic-quality or reduced-resolution version of the medical image, one CAD marker for each CAD detection. Substantial effort and attention has been directed to increasing the analysis capabilities of CAD systems, resulting in ever-increasing amounts of information that is available to the radiologist for review.

Thousands of CAD systems for conventional x-ray mammography are now installed worldwide, and are used to assist radiologists in the interpretation of millions of mammograms per year. X-ray mammography CAD systems are described, for example, in U.S. Pat. No. 5,729,620, U.S. Pat. No. 5,815,591, U.S. Pat. No. 5,917,929, U.S. Pat. No. 6,014,452, U.S. Pat. No. 6,075,879, U.S. Pat. No. 6,301,378, and U.S. Pat. No. 6,574,357, each of which is incorporated by reference herein. Application of CAD algorithms to one or more of tomosynthesis projection images and tomosynthesis reconstructed images for use in conjunction with breast x-ray tomosynthesis systems has been proposed in U.S. Pat. No. 6,748,044, and U.S. Pat. No. 7,218,766, each of which is incorporated by reference herein.

However, in progressing from conventional x-ray mammography to breast x-ray tomosynthesis imaging, practical issues arise with regard to the rising volume of data requiring review by the radiologist. Whereas there are usually just four conventional x-ray mammogram images per patient, there can be hundreds of tomosynthesis reconstructed image slices (e.g., 40-60 slices for each of the four views). As more visual information becomes available, an important challenge is to present such information to the radiologist effectively and efficiently such that screening for abnormalities can be done thoroughly and effectively, and yet in a reasonable time to be practical, and diagnostic assessment can also be facilitated. Of particular importance is the manner in which an image review workstation displays CAD markers to the radiologist for the large stack of tomosynthesis reconstructed images, it being desirable that the CAD markers not be overly obtrusive on their corresponding image while also not being readily overlooked. The visual solution should simultaneously resolve these goals in conjunction with other beneficial goals, such as limiting the number of attention-sapping off-image gadgets to a workable minimum. Even subtle differences involving a few saved eye movements or a few saved hand strokes, keystrokes, or mouse cursor movements can lead to substantially better efficiency, stamina, and/or accuracy on the part of the radiologist.

As used in this patent specification, the notation Mp refers to a conventional x-ray mammogram as captured by a digital flat-panel detector, as As used in this patent specification, the notation Mp refers to a conventional x-ray mammogram as captured by a digital flat-panel detector, as digitized from a film-screen cassette detector, and/or as processed to prepare it for display to the radiologist or for storage. The notation Tp refers to a tomosynthesis projection image that is similarly two-dimensional but is taken at a respective tomosynthesis angle between the breast and the origin of the imaging x-rays (typically the focal spot of an x-ray tube), and also encompasses the image as acquired as well as the image after being processed for display or for some other use. The notation Tr refers a tomosynthesis reconstructed image that is mathematically reconstructed from images Tp represents a slice of the breast as it would appear in a projection x-ray image of that slice at any desired angle, not only at an angle used for Tp or Mp images. In addition, a Tr image can represent a slice that conforms to any desired surface such as a flat or curved plane. Moreover, the process of reconstructing Tr images can use Mp images in addition to using Tp images or instead of one or more Tp images. The terms Tp, Tr and Mp also encompasses information, in whatever form, that is sufficient to describe such an image for display, further processing, or storage. The images Mp, Tp and Tr typically are in digital form before being displayed, and can be defined by information identifying properties of each pixel in a two-dimensional array of pixels although other ways to describe the images can be used as well or instead. The pixel values typically relate to respective measured or estimated or computed responses to x-rays of corresponding volumes in the breast (voxels or columns of tissue). A Tr image can represent a thin slice of a breast, in which case it may consist of pixel values representing respective voxels (volume elements) of the breast that are in a single layer or a few layers, or a Tr image may represent a thicker slice of the breast, in which case the pixel values of the thick-slice Tr image are calculated using known techniques such as, without limitation, a normalized projection of the pixels of several contiguous thin-slice images onto an image plane, a MIP (maximum intensity projection), or some other way of combining the pixel values representing several thin-slice images. As a non-limiting example, a thin-slice Tr image can represent a 1 mm thick slice of the imaged breast and a thick-slice Tr image can represent a 5-20 mm thick slice of the breast. Thus, when a breast is compressed for x-ray imaging to a thickness of 5-6 cm, there can be 50-60 thin-slice Tr images and 3-12 thick-slice Tr images.

Described in this patent specification are methods, systems, and related computer program products for processing and displaying CAD results to a user (e.g., a radiologist) in conjunction with breast x-ray tomosynthesis data in a manner that resolves several issues facing the user during review of such a large data set, including the need to recognize the existence and locations of CAD markers on a relatively small number of Tr images among a relatively large stack of Tr images, while not having inordinate amounts of attention devoted to searching for those CAD markers, without having an inordinate number of off-image eye movements, and without an inordinate amount of Tr image content obscured by annotation content. For example, in one preferred embodiment, a plurality of Tr images representative of slices of a breast having selected orientations and thicknesses is received, and CAD information is received identifying a detection-containing one of the Tr images and a coordinate location thereon at which a CAD detection marker is to be displayed. An ordered sequence of the Tr images is displayed to the user such that the user is allowed to sequentially page therethrough, the ordered sequence including the detection-containing Tr image. The ordered sequence of Tr images further includes at least one Tr image nearby the detection-containing Tr image with respect to the ordered sequence, the nearby Tr image not being detection-containing with respect to the identified coordinate location. When the detection-containing Tr image is displayed, the CAD detection marker is displayed thereon at the identified coordinate location. When the nearby Tr image is displayed, a CAD proximity marker is displayed thereon at the identified coordinate location, the CAD proximity marker not itself being indicative of a CAD detection on the nearby Tr image, but rather for encouraging user attention toward the identified coordinate location of the detection-containing Tr image, for discouraging user oversight of the CAD detection marker thereon when paging therethrough. Preferably, the CAD proximity has a noticeably different size than the CAD detection marker.

For one preferred embodiment, a CAD proximity marker is displayed on each of a plurality of nearby Tr images that are in an immediate neighborhood of the detection-containing Tr image, and the CAD proximity markers are all of noticeably different size relative to each other and to the CAD detection marker. Navigating toward the detection-containing Tr image (e.g., by mouse click, scroll wheel turn, arrow key click, or other paging command), the user pages depthwise from a farthest of the nearby Tr images to a closest of the nearby Tr images, the CAD proximity markers varying in size with each successive image and paging command. In one preferred embodiment, the CAD proximity markers are chirped in size, for example largest to smallest from the farthest nearby Tr image to the closest nearby Tr image. Advantageously, due to keen second-order motion perception in human peripheral vision, the presence of the CAD finding and its location on the display screen is readily noticed and perceived by the radiologist, even when the radiologist has been focusing on a different part of the display screen. Moreover, in many cases, the radiologist may so notice and perceive the presence of the CAD finding, and then continue to track their depthwise paging progression toward the detection-containing Tr image in their peripheral vision even as they continue to focus on a different part of the display.

In other preferred embodiments, further information is conveyed to the user by the CAD proximity markers without additional screen clutter. In one example, a paging behavior of the user, such as the user's paging rate toward or away from the detection-containing Tr image, is detected and instantly used to vary the displayed size of the CAD proximity markers. Thus, for example, if the user is paging very rapidly through the stack of Tr images, thereby increasing the likelihood they might miss the CAD detection marker on the detection-containing Tr image, the CAD proximity markers are made larger and more visible to ensure that the presence of the CAD detection marker is perceived during the fast paging process. However, if the use is paging very slowly, the CAD proximity markers are made smaller and less obtrusive, because it is less likely that the presence of the CAD detection marker will be overlooked. Other useful variations to the size and/or shape of the CAD proximity markers for achieving useful yet non-obtrusive information conveyance, including those described further hereinbelow, are within the scope of the preferred embodiments.

BRIEF DESCRIPTION OF THE DRAWINGS

FIG. 11 illustrates a review workstation display according to a preferred embodiment.

DETAILED DESCRIPTION

Figure 1:
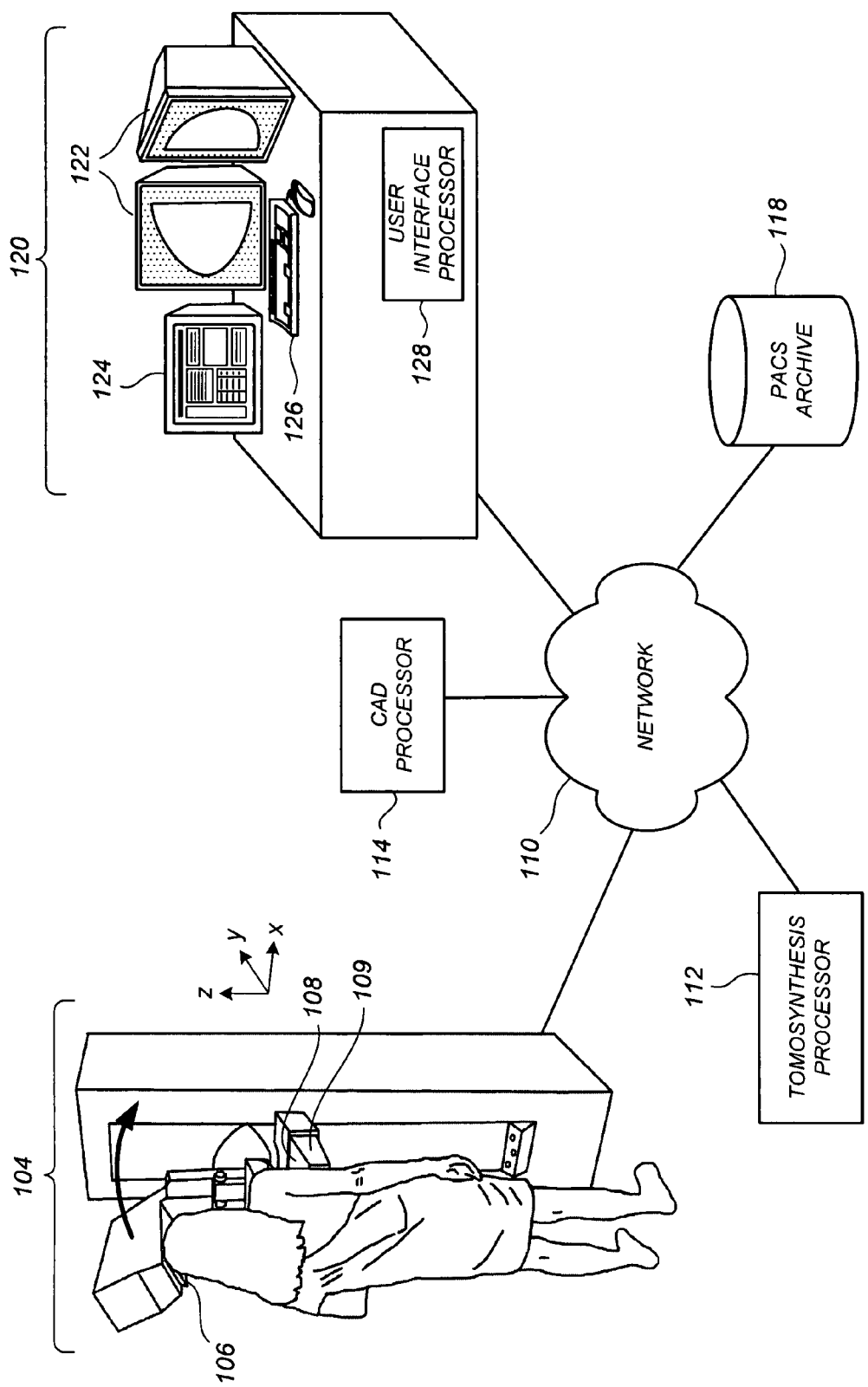
FIG. 1 illustrates a conceptual diagram of a breast x-ray tomosynthesis imaging environment including a review workstation for interactive display of breast x-ray tomosynthesis and related computer-aided detection (CAD) information according to a preferred embodiment.

FIG. 1 illustrates a conceptual diagram of a medical imaging environment for which one or more of the preferred embodiments is particularly suited. Shown in FIG. 1 is a network 110, which may be a HIS/RIS (Hospital Information System/Radiology Information System) network, to which is coupled a breast x-ray tomosynthesis acquisition device 104, which can be dedicated for breast x-ray tomosynthesis or combined with conventional x-ray mammogram functionality. The acquisition device 104 includes an x-ray source 106 projecting x-rays toward a patient's breast that is supported on a breast platform 108. An x-ray imager 109 such as a flat panel, direct conversion imager available from Hologic, Inc. generates projection image data such as data defining images Mp and/or Tp. With respect to a three-dimensional coordinate system as illustrated in FIG. 1, in which an x-z plane corresponds at least roughly to a coronal plane of the patient and the y-direction extends outward from the patient, the x-ray source 106 is mounted for arcuate movement in the x-z plane around breast platform 108 (for example, between −15 degrees and +15 degrees relative to a y-axis). Tomosynthesis projection images Tp are be taken at a number of different angles for that specific orientation of breast platform, such as a generally CC orientation (as illustrated in FIG. 1) or a generally MLO orientation. The x-ray imager 109 can be stationary but preferably it also moves relative to breast platform 108, in a specified synchronous relationship to x-ray source 106, preferably in a manner that keeps the imaging plane at the same angle to the imaging x-ray beam. The x-ray source 106 and x-ray imager 109 are controlled by an acquisition control unit (not shown) of the acquisition device 104.

The Tp images acquired by the x-ray imager 109 are then processed by a tomosynthesis processor 112 according to a tomosynthesis reconstruction algorithm to form tomosynthesis reconstructed images Tr. A computer-aided detection (CAD) processor 114 coupled to the network 110 receives the acquired image information and processes the received information to detect anatomical abnormalities in the breast using one or more CAD algorithms. Notably, the information processed by CAD processor 114 need not be limited to the Tr and/or Tp images received from units 104 and 112, but may also include conventional x-ray mammogram information, non-image data such as patient demographics and family history information, prior year Tr/Tp images, images from other modalities, and so on as may facilitate the abnormality detection process. For any particular suspected abnormality meriting the attention of the radiologist according to the criteria of the CAD algorithm, also termed herein a CAD finding or a CAD detection, the CAD processor identifies the Tr image(s) and coordinate location(s) thereon associated with that suspected abnormality, or provides information from which those Tr image(s) and coordinate location(s) can be determined. The tomosynthesis image information is then viewed in conjunction with the associated CAD information at a radiology review workstation 120 by the radiologist, who makes a clinical determination therefrom. The clinical determination can be in relation to screening, diagnosis, follow-up, or any of a variety of other activities Preferably, the various medical images and related information are communicated according to the DICOM (Digital Imaging and Communications in Medicine) standard and the network 110 supports the TCP/IP protocol, which is used as the transport protocol for the DICOM standard. Also coupled to the network 110 is a PACS (Picture Archiving and Communication System) archive 118, generally representing a repository for medical information associated with the medical imaging environment, including both current and archived images, current and archived CAD results, radiology reports for completed cases, and so forth.

Review workstation 120 comprises a diagnostic display 122 and an administrative display 124. Administrative display 124 is used for input and output of a wide variety of information that may be associated with a particular set of medical images (e.g., listings, tables, plots, text descriptions, etc), as well as for system installation, maintenance, updating, and related tasks. Also provided are user input devices 126 (e.g., keyboard, mouse, trackball, pointer, etc.) that receive user commands, and a user interface processor 128 that drives the displays 122 and 124 responsive to those user commands. Among other well-known user interface features provided by the review workstation 120, such as zooming, panning, user-annotating, retrieving, storing, etc., are navigation and paging functions that are particularly relevant for purposes of the present disclosure and described further hereinbelow. It is to be appreciated that the user interface features described herein are broadly applicable for a variety of user interface hardware implementations and that many variations are within the scope of the preferred embodiments. By way of example, whereas at least one example herein illustrates paging commands as being mouse clicks, any user input that instantiates a like paging operation (ranging from keystroke sequences to touchscreen inputs to virtual reality glove movement) is within the scope of the preferred embodiments.

Notably, the medical imaging environment of FIG. 1 is presented by way of example only and is not intended to limit the scope of the preferred embodiments to this particular scenario. By way of example, different combinations of the devices of FIG. 1 can be placed adjacently to each other or integrated into the same hardware boxes without departing from the scope of the preferred embodiments. By way of still further example, the network 110 can be a wide-area network with the different nodes being distributed throughout a city, a country, or the world. Alternatively, and by way of still further example, some or all of the transfer of digital information can be achieved by physical transfer of disks, memory sticks, or other digital media devices without departing from the scope of the preferred embodiments. In view of the present disclosure, a person skilled in the art would be able to construct such plug-ins or other software packages capable of achieving the described user interfaces and processing functionalities without undue experimentation, using publicly available programming tools and software development platforms.

Figure 2:
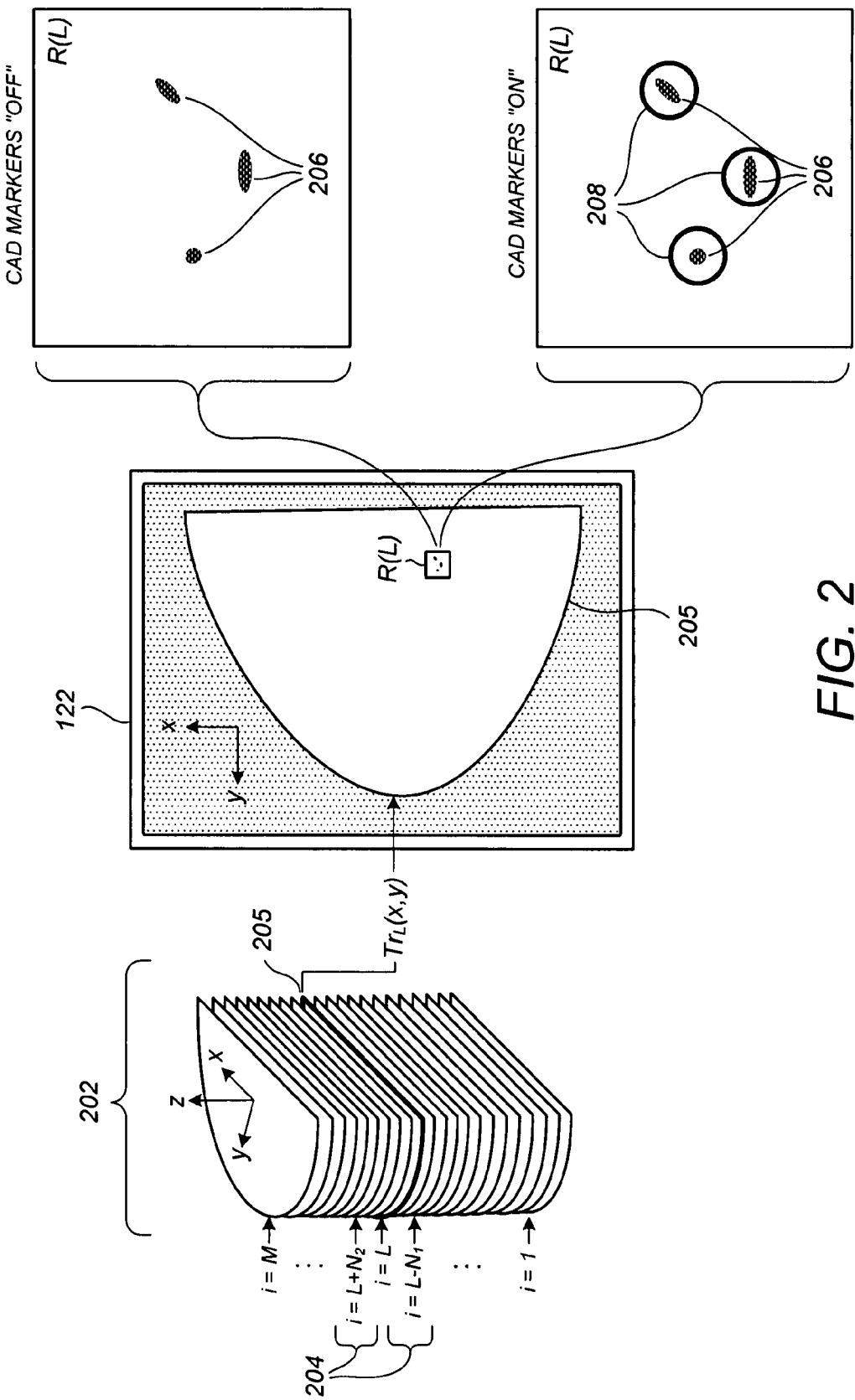
FIG. 2 illustrates a perspective view of a notional stack of tomosynthesis reconstructed (Tr) images, a review workstation display, and close-up views of the review workstation display according to a preferred embodiment.

FIG. 2 illustrates a perspective view of a notional stack 202 of Tr images $Tr_i(x,y)$, $\{i=1, \ldots, M\}$ reconstructed from a plurality of Tp images. For clarity of disclosure, and without loss of generality, the examples herein are illustrated for the simple case of a CC view of a right breast compressed against a horizontal breast platform corresponding to the x-y direction, and the Tr images $Tr_i(x,y)$ corresponding to planar, horizontal breast slices at a height $z_i$ above the breast platform. It is to be appreciated that, in a more general case, the notional image stack 202 could correspond to any of a variety of different orientations and breast slice shapes/thicknesses. Also illustrated in FIG. 2 is the diagnostic display 122 displaying an $L^{th}$ one of the Tr images 205 which, in this example, contains a CAD finding at a lateral coordinate location thereon in a small region R(L) as shown, and which is referenced herein as a detection-containing Tr image.

Further illustrated in FIG. 2 at the notional stack 202 is an immediate neighborhood 204 of the detection-containing image 205, the neighborhood 204 consisting of $N_1$ Tr images immediately below the detection-containing image 205 and $N_2$ Tr images immediately above the detection-containing image 205. The neighborhood 204 contains $(N_1+N_2)$ member Tr images, with at least one of $(N_1+N_2)$ being greater than zero. In the event both $N_1$ and $N_2$ are greater than zero, the neighborhood 204 can be expressed as $T_k(x,y)$, $\{k=L-N_1, \ldots, L-1, L+1, \ldots, L+N_2\}$. In the example of FIG. 2, it is presumed that none of the Tr images in the neighborhood 204 are detection-containing with respect to locations in or near the region R(L).

Also illustrated in FIG. 2 are close-up views of the small region R(L) in each of a "CAD Markers Off" mode and a "CAD Markers On" mode. For one preferred embodiment, in a manner similar to common clinical practice under FDA guidelines for conventional x-ray mammography, the user is given the ability to select between the "CAD Markers Off" mode and the "CAD Markers On" mode and is expected to review the images with "CAD Markers Off" prior to reviewing the images with "CAD Markers On." It is not necessarily a certainty that these practices and guidelines will be extended to a breast x-ray tomosynthesis image review environment in which there is much more data to be reviewed. Without loss of generality, the "CAD Markers On" mode is presumed to be active in the examples hereinbelow unless stated otherwise.

As used herein, "CAD detection marker" refers to a two-dimensional graphical annotation overlaid on a two-dimensional medical image that draws attention to the lesion pixels that are displayed in that specific medical image. CAD detection markers typically include shapes drawn around the lesion pixels such as circles, squares, triangles, etc., but can also be implemented by "artificial" coloration or brightening of the lesion pixels themselves, or "artificial" brightness/contrast offsets in the shapes of circles, squares, etc. that draw attention to the lesion pixels, where "artificial" refers to inducing these visual variations due to CAD analysis results and not simply as part of some other image processing algorithm applied image-wide. As used herein, the term "CAD marker" refers generically to either "CAD detection markers" or "CAD proximity markers," the latter term being described further below.

In accordance with this terminology, shown in FIG. 2 in the region R(L) are lesion pixels 206 which correspond, for example, to several microcalcifications visible in the detection-containing image Tr image 205, and which appear the same in both the "CAD Markers Off" image and "CAD Markers On" image. Also shown, in the "CAD Markers On" image are circular CAD detection markers 208, which draw attention to the lesion pixels 206.

Generally speaking, each of the Tr images in the notional stack 202 can be very large in both pixel count and physical size as displayed to the radiologist in clinical practice. By way of example, the image in diagnostic display 122 of FIG. 2 may be 2048 pixels in the x-direction and 1792 pixels in the y-direction, and can physically extend more than 16 inches (41 cm) in the x-direction and 13 inches (33 cm) in the y-direction for screening and/or diagnostic quality viewing. In contrast, suspected lesions can be very small, for example, a detected microcalcification can be less than 0.5-1 mm in diameter, and it is often desired that the associated CAD detection markers not be much larger than that (perhaps 5-10 mm, so that the surrounding tissue is not unnecessarily obscured or cluttered). Although such smallness (CAD detection marker size relative to overall image size) is typically not a problem for conventional x-ray mammograms because there are typically only four (4) Mp images to review, this smallness can become problematic if there are dozens and even hundreds of Tr images to review.

As used herein, paging through the notional stack 202 of two-dimensional images refers to viewing a time sequence of the images $Tr_i(x,y)$ in lateral registration with each other on the display 122 while causing the index "i" to increase and decrease in steps of unity responsive to a user paging command. The paging command can be a mouse click on a particular display button, a stroke of an up/down arrow key, etc. Stated another way, if a current image "i" corresponds to the vertical position of a virtual person in the notional stack 202, then paging commands are represented by upward and downward steps of that person in the notional stack 202. Stated still another way, paging through the notional stack 202 is analogous to watching a cine presentation of the images $Tr_i(x,y)$ that is manually driven on a per-frame basis. As used herein, paging through the notional stack 202 represents one type of navigation through the notional stack 202, the term navigation referring more broadly to a wider range of travel types through the notional stack (automated cine movement or continuously morphable presentation, for example) while the image associated with the current level is being displayed.

Figure 3:
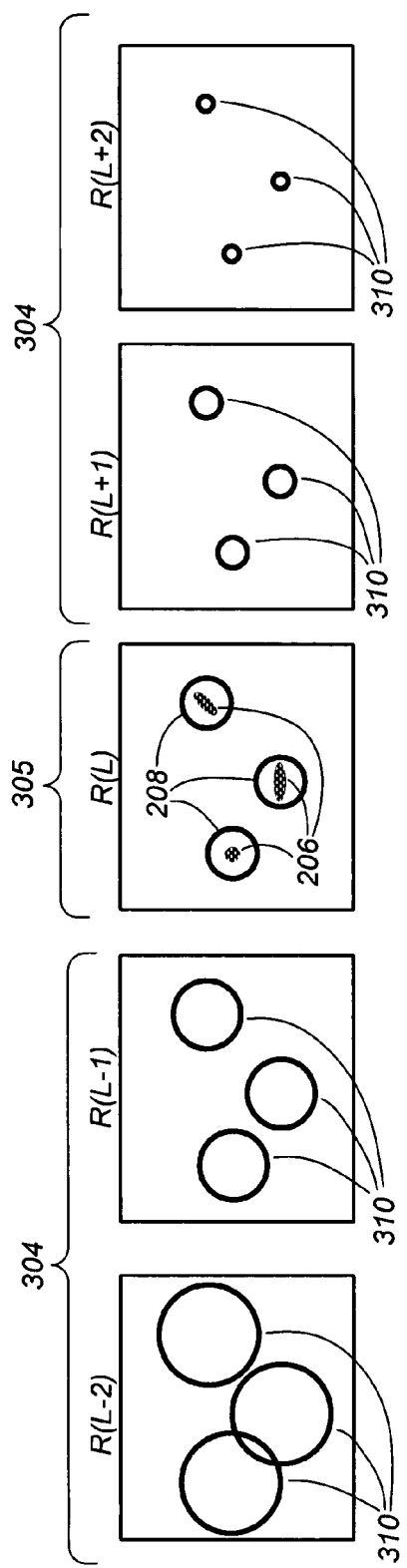
FIGS. 3-8 illustrate close-up views of ordered sequences of Tr images as displayed to a user in accordance with one or more preferred embodiments.

FIG. 3 illustrates a close-up view of regions R(i) of successive Tr images $Tr_i(x,y)$ as the user is paging depthwise (upward in this example) in the notional stack 202 through the neighborhood 204 and detection-containing Tr image 205 according to a preferred embodiment. For example, if the display is currently presenting R(L−1), either in a zoomed mode or as part of the entire image $T_{L-1}(x,y)$, and then the user enters an "up arrow" paging command, the image R(L) replaces the image R(L−1) on the display monitor, appearing at the same lateral location and the same zoom level as the image R(L−1) appeared when the "up arrow" command was entered. If the user enters a "down arrow" page command, then the image R(L−2) replaces the image R(L−1) on the display monitor. In FIG. 3, the images R(i) corresponding to the neighborhood 204 are termed neighborhood images 304, while the image(s) R(i) corresponding to the detection-containing Tr image 205 are termed detection-containing image(s) 305.

For the example of FIG. 3, the size of the neighborhood 204 is four Tr images, two of them below ($N_1=2$) and two of them above ($N_2=2$) the detection-containing Tr image 205. However, a wide variety of values for each of $N_1$ and $N_2$ are within the scope of the preferred embodiments. For a stack of M=44 images, examples of suitable value combinations can include ($N_1=2$, $N_2=1$), ($N_1=3$, $N_2=0$), ($N_1=5$, $N_2=5$), ($N_1=0$, $N_2=5$), ($N_1=8$, $N_2=4$), and ($N_1=10$, $N_2=10$).

According to a preferred embodiment, CAD proximity markers 310 are displayed on each of the neighborhood images 304. As used herein, "CAD proximity marker" refers to a two-dimensional graphical annotation overlaid on a two-dimensional medical image, wherein that medical image does not itself contain a CAD detection or lesion pixels near the CAD proximity marker, but rather the CAD detection/lesion pixels are contained in a nearby two-dimensional medical image of a notional stack of such two-dimensional medical images that is being navigated through. The neighborhood images 304 do not themselves contain CAD detection markers, but rather contain CAD proximity markers 310 designed to draw user attention to the identified location at which the CAD detection marker 208 is about to be displayed (or has just been displayed) in the paging process. The CAD proximity markers 310 may, or may not, visually resemble the CAD detection marker 208, although in a preferred embodiment are all of noticeably different size relative to each other and to the CAD detection marker 208. Preferably, the total size ($N_1+N_2$) of the neighborhood 204 should be less than 25 percent (for one preferred embodiment) or less than 10 percent (for another preferred embodiment) of the total number of Tr images corresponding to a particular view of one breast, to keep overall obtrusiveness of the CAD proximity markers at modest levels.

In the particular example of FIG. 3, the CAD proximity markers 310 are chirped in size from largest at one end of the neighborhood 304 to smallest at the other end. Among other advantages, this kind of sizing of the CAD proximity markers (i.e., larger on one side of the CAD detection marker and smaller on the other side) provides the other with a clue as to whether they need to move "forward" or "backward" from their current Tr image to arrive at the detection-containing Tr image. If the user pages "upward" in the notional image stack 202, the CAD proximity markers 310 go from largest to smallest, whereas if the user pages "downward" in the notional image stack 202, the CAD proximity markers 310 go from smallest to largest. In an alternative embodiment (not shown), the CAD proximity markers are direction-dependent such that they chirp from large to small regardless of whether the user is paging upward or downward. Notably, unlike CAD detection markers than are static and therefore amenable to "burning in" to the diagnostic image (see, for example, the commonly assigned U.S. Pat. No. 6,909,795), direction-dependent and/or velocity-dependent CAD proximity markers cannot be burned into their associated images because their visual characteristics will depend on the current direction or velocity of the paging.

Advantageously, when viewing the full Tr images on an actual full-size display monitor in clinical practice, the paged succession of the CAD proximity markers 310 and the CAD detection marker 208 provides a unique and compelling user experience that allows the region R(i) to be readily noticeable, but at the same time not attention-sapping. When the user is focusing on a different part of the monitor during the paging process, the continuous/staggered paged succession of differently-sized markings appeals to second-order motion perception in human peripheral vision away from the fovea and thus its presence and location are readily noticed. Also, especially as the radiologist grows accustomed to this user interface, they may even (i) notice and perceive the presence of the CAD finding, and then (ii) continue to track their depthwise paging progression toward that CAD finding in their peripheral vision even as they continue to focus on a different part of the display.

Figure 4:
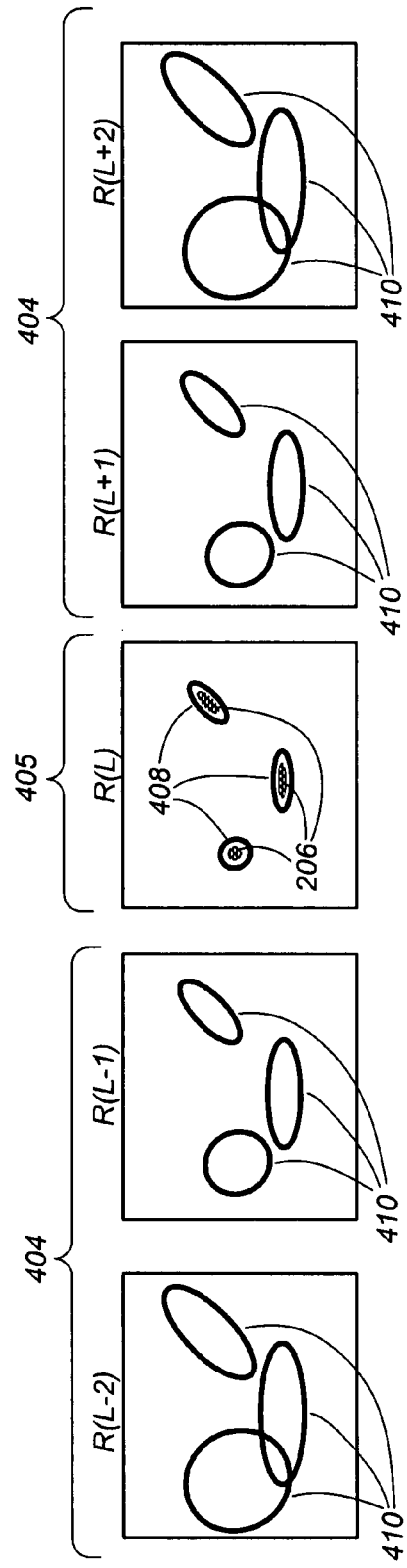

FIG. 4 illustrates a progression of CAD proximity markers 410 and a CAD detection marker 408 as the user pages through a detection-containing image 405 and a plurality of associated neighborhood images 404 according to another preferred embodiment. Here, the CAD proximity markers 410 are conformal in shape to the CAD detection marker 408, which are in turn conformal to the patterns formed by the lesion pixels 206. As such, the CAD proximity markers 410 portend at least some amount of information about the lesions additional to the fact of their impending (or recent) display. Also, the CAD proximity markers 410 are all greater in size than the CAD detection marker 408, and are symmetrically sized relative to their sequential order such that the user sees the same size progression regardless of whether they are "traveling" in an upward or downward direction toward the detection-containing Tr image in the notional stack 202.

Figure 5:
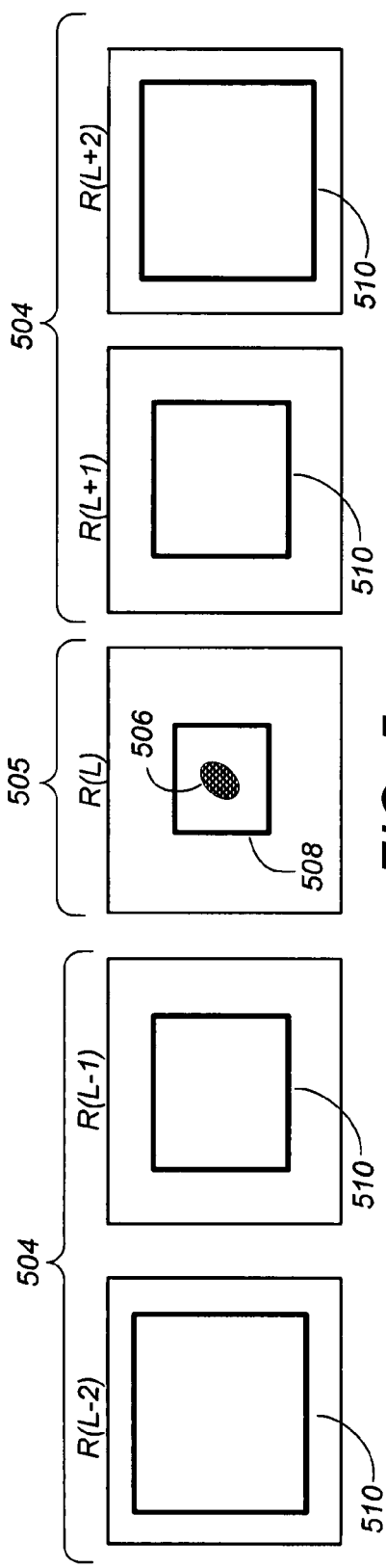

FIG. 5 illustrates a progression of CAD proximity markers 510 and a CAD detection marker 508 as the user pages through a detection-containing image 505 and a plurality of associated neighborhood images 504 according to another preferred embodiment. For this example the detected lesion can be a small density, as indicated by the lesion pixels. The CAD detection marker 508 is rectangular. The CAD proximity markers 510 are conformal in shape to, and greater in size than, the CAD detection marker 508, and are symmetrically sized relative to their sequential order.

It is to be appreciated that the preferred embodiments are readily applicable when the CAD finding in question relates to a lesion that extends across multiple Tr images such that there are CAD detection markers and lesion pixels on multiple adjacent Tr images. In such case, the CAD proximity markers appear in the one or more Tr images positioned in the notional Tr image stack just prior to the first detection-containing Tr image and/or just after the final detection-containing Tr image for that particular lesion.

Figure 6:
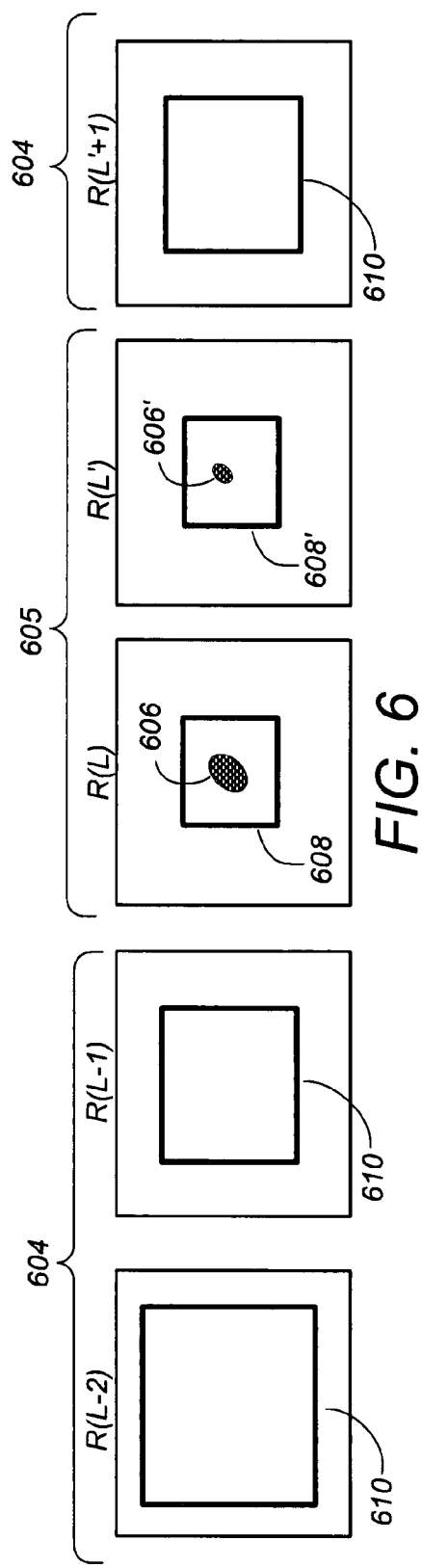

FIG. 6 illustrates a progression of CAD proximity markers 610 corresponding to such scenario, wherein the lesion pixels of a CAD detection extend across more than one of the Tr images in the notional image stack 202. Shown in FIG. 6 are a plurality of detection-containing images 605 containing lesion pixels 606 and 606' and CAD detection markers 608 and 608'. Here, the CAD proximity markers 610 are designed in a manner similar to the scenarios of FIGS. 3-5, except that the neighborhood 604 of non-lesion-containing Tr images now straddles a greater number of lesion-containing images 605. For one preferred embodiment, each of the CAD proximity markers 610 has a size dimension larger than a largest-sized one of the CAD detection markers 608 and 608'.

Figure 7:
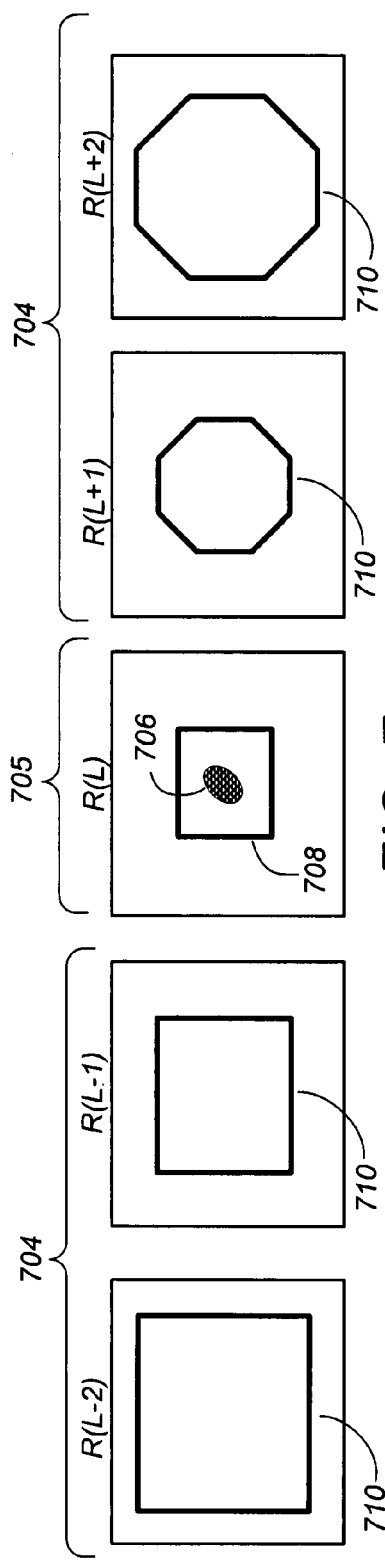

FIG. 7 illustrates a progression of CAD proximity markers 710 and a CAD detection marker 708 as the user pages through a detection-containing image 705 and a plurality of associated neighborhood images 704 according to another preferred embodiment. Here, the CAD proximity markers 710 are shaped differently for neighborhood images 704 on different sides (sequentially) of the detection-containing image 705, which can advantageously provide a symbolic signal to the radiologist as to the side from which the detection-containing image 705 is being approached (i.e., the side from which the detection-containing Tr image $T_L(x,y)$ is being approached in the notional stack 202).

Figure 8:
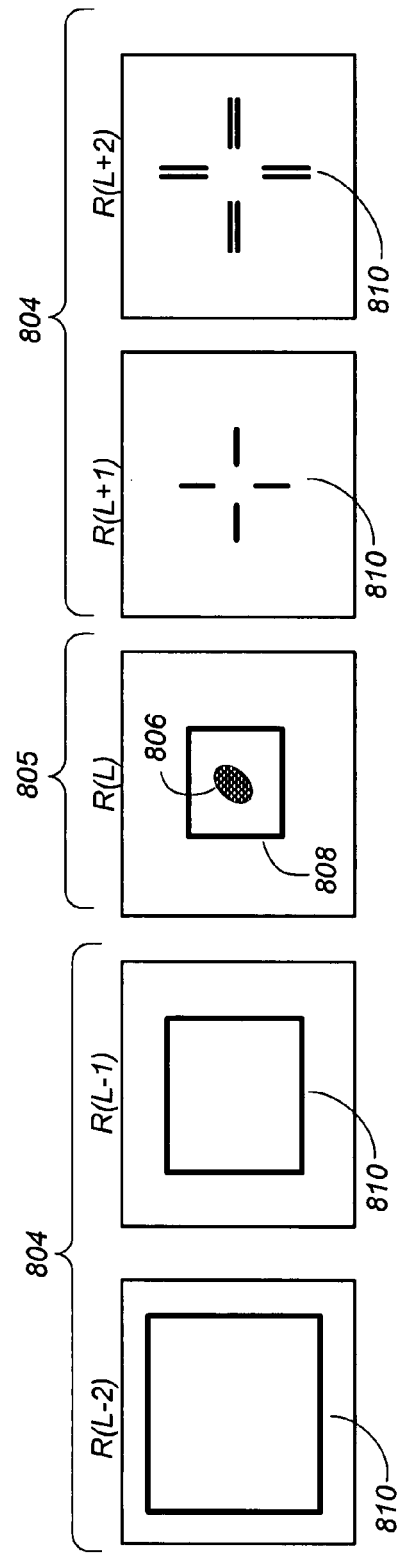

FIG. 8 illustrates a progression of CAD proximity markers 810 and a CAD detection marker 808 as the user pages through a detection-containing image 805 and a plurality of associated neighborhood images 804 according to another preferred embodiment. Here, the CAD proximity markers 810 are shaped "alarmingly" differently for neighborhood images 804 on a different sides of the detection-containing image 805. For another embodiment (not shown), this can be combined with the above-described direction-dependent CAD proximity marker scheme such that, for example, whenever the user is paging toward the detection-containing lesion (regardless of which side they are on) the CAD proximity markers are square-shaped, and whenever they are paging away from the detection-containing lesion from they see the "alarmingly" different CAD proximity markers.

Figure 9A:
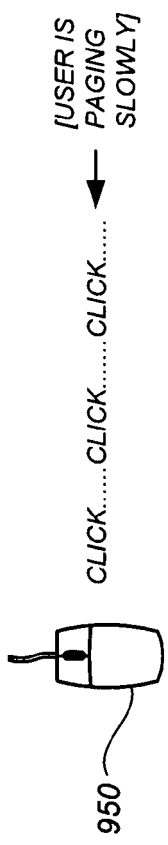
FIG. 9A illustrates a close-up view of an ordered sequence of Tr images as displayed to a user in accordance with a preferred embodiment when the user is paging slowly therethrough.
Figure 9B:
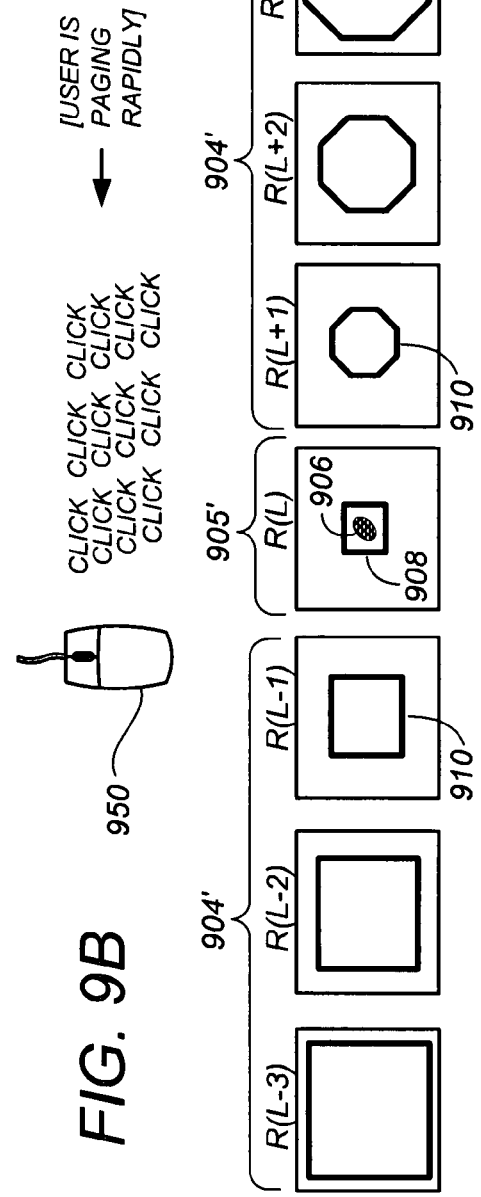
FIG. 9B illustrates a close-up view of an ordered sequence of Tr images as displayed to a user in accordance with a preferred embodiment when the user is paging rapidly therethrough.

FIGS. 9A-9B illustrate examples of (i) velocity-dependent or paging rate-dependent sizing of CAD proximity markers, as well as (ii) velocity-dependent or paging rate-dependent sizing of the neighborhood for which CAD proximity markers are displayed. These features can be used together or separately without departing from the scope of the preferred embodiments. With respect to FIG. 9A, when the user is paging slowly (as indicated graphically by the mouse 950 and sparse "click" terms), and therefore has more time to view each image, there are four neighborhood images 904 for which CAD proximity markers 910 are shown, and the size differential among the CAD proximity markers 910 is relatively slight. With respect to FIG. 9B, when the user is paging rapidly (as indicated graphically by the density of "clicks" near the mouse 950), and therefore has less time to view each image, there are six neighborhood images 904' for which CAD proximity markers 910 are shown, and the size differential among the CAD proximity markers 910 (as well as between the CAD proximity markers 910 and the CAD detection marker 908) is more extreme. In another preferred embodiment (not shown), when the user is paging so slowly as to be in static or quasistatic review of the images, the size of the neighborhoods can optionally be taken to zero, in which the CAD proximity markers 910 would be omitted entirely from display. In other preferred embodiments (not shown), the visual cues provided by the size-varying CAD proximity markers are further enhanced by use of progressively different textures for the CAD proximity marker lines and/or the use of gradually or drastically varying grayscales or other coloration of the CAD proximity markers, both relative to each other and/or relative to the CAD detection markers.

Figure 10:
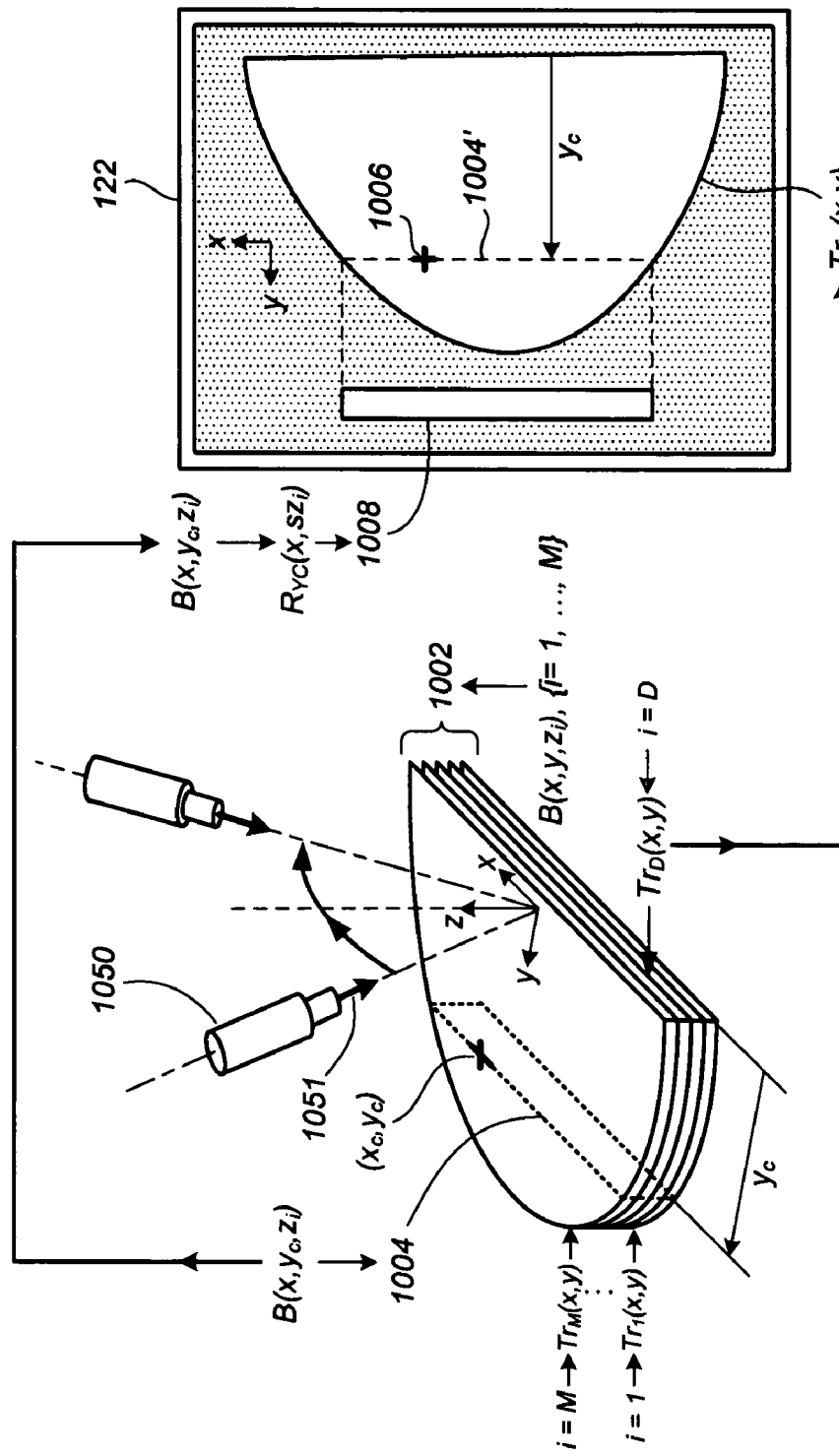
FIG. 10 illustrates a perspective view of a three-dimensional breast volume as formed by a notional stack of a Tr images and a review workstation display according to a preferred embodiment.

FIG. 10 illustrates a perspective view of a three-dimensional breast volume 1002 as formed by a notional stack of a Tr images $Tr_i(x,y)$, $\{i=1, \ldots, M\}$, along with the review workstation display 122 displaying a ribbon image 1008 according to a preferred embodiment. Despite advancements in the field of tomosynthesis reconstruction techniques, the relatively sparse number of tomosynthesis projection images taken and the relatively low number of x-ray photons used (e.g., in comparison to higher-dose CT imaging procedures) can result in the presence of certain artifacts in the reconstructed images that degrade image quality. It has been found, however, that a particular tomosynthesis reconstruction artifact associated with a particular imaging geometry and with small anatomical densities (such as microcalcifications) can yield a relatively "stable" artifact that can be useful in analysis of breast x-ray tomosynthesis data.

Illustrated above the breast volume 1002 in FIG. 10 is a notional x-ray source 1050 and x-rays 1051 emanating therefrom emulative of the x-ray source 106 of FIG. 1, supra, relative to the physical breast volume. In particular, where the breast is flattened along a breast platform representative of the x-y direction, the x-rays 1051 originate from a plurality of angles relative to the y-axis as the x-ray source is rotated therearound in the x-z plane. After the raw Tp data is processed to compute the Tr images that form the breast volume 1002, that breast volume can be viewed in different ways, including displaying one or more two-dimensional Tr images, such as a $D^{th}$ image $Tr_D(x,y)$ shown in FIG. 10. It has been found that a strip-like two-dimensional image formed by a cutting plane 1004 that is substantially parallel to the x-z plane and has a fixed coordinate distance $y_c$ in the direction normal to the x-z plane tends to reliably show a star-like artifact for small densities, such as microcalcifications, that may be contained along that plane in the breast volume. The star-like artifact is particularly noticeable when the strip-like image is "collapsed" to a small strip, or ribbon, with respect to the z-direction in which the breast was compressed.

Thus, according to one preferred embodiment, a user-established cursor position 1006 at $(x_c, y_c)$ is detected on the $D^{th}$ image $Tr_D(x,y)$, and a two-dimensional ribbon image 1008 is displayed adjacent thereto, being separated therefrom in the y-direction and in registration therewith along the x-direction. The ribbon image 1008 can be expressed as $R_{YC}(x,sz_i)$, $\{i=1, \ldots, M\}$, and corresponds to an x-z cut plane $B(x,y_c,z_i)$ of the notional data volume 1002. Preferably, "s" is a scaling factor selected such that the ribbon image 1008 appears substantially collapsed in the z-direction in comparison to the actual height of the x-z cut plane $B(x,y_c,z_i)$ in the breast relative to the actual width of the breast in the x-direction. If the user moves the cursor position 1006 strictly in the x-direction on the display 122, there is no change in the ribbon image 1008, because the offset $y_c$ has stayed the same. However, the content and vertical extent of the ribbon image 1008 in FIG. 10 varies (preferably in real time) as the user moves the cursor position 1006 in the y-direction.

FIG. 11 illustrates a close-up view of an area "A" of the display 122 of FIG. 10 when the user has placed the cursor on a small density 1102. Evident in the ribbon image 1008 is a star-like artifact 1104. Although the star-like artifact 1104 would not be present for "perfect" tomographic reconstructions, its presence and characteristics can be used in detecting and/or analyzing the small density 1102. Optionally, a numerical processing algorithm can be applied to the ribbon image 1008 that emphasizes starlike patterns therein prior to display. Also evident in the close-up view of area "A" is an artificial marker line 1106 that corresponds to depth of the $D^{th}$ image $Tr_D(x,y)$ in the notional image stack 1002 that can serve as a navigational aid as the user pages through the notional stack of Tr images.

Whereas many alterations and modifications of the preferred embodiments will no doubt become apparent to a person of ordinary skill in the art after having read the foregoing description, it is to be understood that the particular embodiments shown and described by way of illustration are in no way intended to be considered limiting. By way of example, in other preferred embodiments, when there are several CAD proximity markers corresponding to several neighborhood Tr images, respectively, alternating ones of the CAD proximity markers may be omitted from display to create a blinking/flashing effect as the user pages through them. In still other preferred embodiments, any particular CAD proximity marker and/or CAD detection marker blinks/flashes intrinsically on its associated Tr image, such that the blinking/flashing occurs even when navigation has halted on that Tr image.

By way of further example, for larger lesions extending across a relatively large multiplicity of Tr images, the advantages of using CAD proximity markers may not be quite as pronounced as for smaller lesions appearing in only a relatively few Tr images. This is because those larger lesions and their multiplicity of CAD detection markers across the multiplicity of Tr images will inherently be more apparent than for smaller lesions and their relatively few CAD detection markers across relatively few Tr images. Thus, in one alternative preferred embodiment, the user is provided with the ability to turn off CAD proximity markers for larger lesions extending across multiple Tr images, as well as the ability to set a threshold for what constitutes such large multiplicity of Tr images. In still another alternative preferred embodiment, the user can pre-select whether a microcalcification cluster that extends across multiple Tr images, but otherwise has a tiny footprint on any particular one of those Tr images, should be considered as a single large lesion or several small lesions for the purposes of CAD proximity markings and/or for purposes of the optional turn-off feature. Thus, reference to the details of the described embodiments are not intended to limit their scope, which is limited only by the scope of the claims set forth below.

What is claimed is:

1. A method for displaying computer-aided detection (CAD) results associated with breast x-ray tomosynthesis data, comprising:
    receiving a plurality of two-dimensional tomosynthesis reconstructed (Tr) images representative of slices of a breast having selected orientations and thicknesses;
    receiving CAD information identifying a detection-containing one of said Tr images and further identifying a coordinate location at which a CAD detection marker is to be displayed thereon;
    interactively displaying said Tr images to a user including allowing the user to sequentially page through an ordered sequence of said Tr images, said ordered sequence including said detection-containing Tr image, said ordered sequence further including at least one Tr image nearby said detection-containing Tr image with respect to said ordered sequence, said nearby Tr image not being detection-containing with respect to said identified coordinate location;
    when displaying said detection-containing Tr image, displaying thereon said CAD detection marker at said identified coordinate location; and
    when displaying said nearby Tr image, displaying thereon a CAD proximity marker at said identified coordinate location, wherein said CAD proximity marker is of noticeably different size than said CAD detection marker;
    whereby said CAD proximity marker, while not indicative of a detection on said nearby Tr image, encourages user attention toward the identified coordinate location of the detection-containing Tr image to discourage user oversight of the CAD detection marker thereon when paging therethrough.

2. The method of claim 1, said ordered sequence of Tr images including a plurality of Tr images in an immediate and adjacent neighborhood of said detection-containing Tr image with respect to the ordered sequence, said plurality of neighborhood Tr images not being detection-containing with respect to said identified coordinate location, the user varying a virtual depth between a virtual closest Tr image and a virtual farthest Tr image when paging through said ordered sequence, the method further comprising:
    when displaying each of said plurality of neighborhood Tr images, displaying thereon a corresponding CAD proximity marker of noticeably different size than said CAD detection marker;
    wherein, for all said neighborhood Tr images on one of a closer end and a farther end of the detection-containing Tr image, said CAD proximity markers are all of noticeably different size relative to each other.

3. The method of claim 2, wherein for all said neighborhood Tr images on said closer or farther end, said CAD proximity markers are noticeably chirped between a largest size farthest from the detection-containing Tr image to a smallest size closest to said detection-containing Tr image, and wherein said smallest-sized CAD proximity marker is of noticeably larger size than said CAD detection marker.

4. The method of claim 3, wherein the size at which at least one of said CAD proximity markers is displayed is at least partially determined according to a paging behavior of the user sensed during said interactively displaying.

5. The method of claim 4, wherein said size at which said at least one CAD proximity marker is displayed is larger when the user is paging more rapidly through said ordered sequence of Tr images and is smaller when the user is paging more slowly through said ordered sequence of Tr images.

6. The method of claim 5, wherein a sensitivity of said displayed size of said at least one CAD proximity marker to said sensed paging behavior is user-settable.

7. The method of claim 3, wherein a depthwise extent of the neighborhood of Tr images for which said CAD proximity markers is displayed also depends upon said sensed paging behavior, said CAD proximity markers being displayed on a greater number of neighborhood Tr images when the user is paging more rapidly through said ordered sequence, said CAD proximity markers being displayed on a lesser number of neighborhood Tr images when the user is paging more slowly through said ordered sequence.

8. The method of claim 2, wherein the CAD proximity markers for all said neighborhood Tr images on said closer end of the detection-containing Tr image are of noticeably different shape type than the CAD proximity markers for all said neighborhood Tr images on said farther end, whereby user attention is drawn to a paging-through of the detection-containing Tr image by virtue of a noticeable change in shape type of said CAD proximity markers.

9. The method of claim 2, wherein for all said neighborhood Tr images on said closer end, said CAD proximity markers are all larger in size than said CAD detection marker and are noticeably chirped largest to smallest toward said detection-containing Tr image, and wherein for all said neighborhood Tr images on said farther end, said CAD proximity markers are all smaller in size than said CAD detection marker and are noticeably chirped largest to smallest away from said detection-containing Tr image.

10. The method of claim 2, wherein each of said CAD proximity markers is shaped conformally to a shape of said CAD detection marker.

11. The method of claim 1, further comprising:
receiving a plurality of tomosynthesis projection images Tp obtained with the breast flattened against a compression paddle defining an x-y plane and with an x-ray source traversing in an arc around an axis parallel to the y-axis in a plane parallel to the x-z plane;
processing said Tp images to compute said plurality of Tr images, wherein each of said ordered sequence of Tr images $Tr_i(x,y)$, $\{i=1, \ldots, M\}$, is representative of a breast slice $B(x,y,z_i)$ at a respective height $z_i$ above said compression paddle, said ordered sequence of Tr images $Tr_i(x,y)$, $\{i=1, \ldots, M\}$, collectively defining a data volume $B(x,y,z_i)$, $\{i=1, \ldots, M\}$;
during said interactively displaying, receiving a user-established cursor position $(x_c, y_c)$ on a displayed one "D" of said Tr images $Tr_D(x,y)$ on the display device; and
displaying on the display device a two-dimensional ribbon image $R_{YC}(x,sz_i)$, $\{i=1, \ldots, M\}$, adjacent to said displayed Tr image $Tr_D(x,y)$, separated therefrom in the y-direction and in registration therewith along the x-direction, wherein said ribbon image $R_{YC}(x,sz_i)$, $\{i=1, \ldots, M\}$, corresponds to an x-z cut plane $B(x,y_c,z_i)$ through said data volume $B(x,y,z_i)$ at said cursor ordinate $y_c$, and wherein "s" is a scaling factor selected such that the ribbon image $R_{YC}(x,sz_i)$, $\{i=1, \ldots, M\}$ appears substantially collapsed in the z-direction in comparison to the x-z cut plane $B(x,y_c,z_i)$;
whereby, when there is a microcalcification or small-density abnormality associated with said CAD detection marker and when said cursor ordinate $y_c$ corresponds to said identified location coordinates, said ribbon image $R_{YC}(x,sz_i)$, $\{i=1, \ldots, M\}$, optimizes visibility of starlike tomosynthesis reconstruction artifacts that may be associated with said abnormality for assisting in user analysis thereof.

12. The method of claim 11, further comprising applying a numerical processing algorithm to said ribbon image $R_{YC}(x, sz_i)$, $\{i=1, \ldots, M\}$, that emphasizes starlike patterns therein prior to said displaying thereof.

13. A system for interactively displaying breast x-ray tomosynthesis data to a user, the data including a plurality of tomosynthesis reconstructed slice images representative of slices of a breast having selected orientations and thicknesses, the data further including computer-aided detection (CAD) information identifying a suspected anatomical abnormality and a coordinate location thereof on a first of said slice images, the system comprising:
a user input unit receiving user navigation commands controlling a virtual depth in a notional stack of said slice images, said virtual depth being upwardly and downwardly movable according to the user navigation commands; and
a display unit displaying said slice images one at a time to the user according to said virtual depth in said notional stack;
wherein, when displaying said first slice image, said display unit displays a CAD detection marker thereon at said identified coordinate location; and
wherein, when displaying a second slice image nearby in said notional stack to said first slice image and not containing suspected abnormalities with respect to said identified coordinate location, said display unit displays on said second slice image a CAD proximity marker at said identified coordinate location that is of noticeably different size than said CAD detection marker.

14. The system of claim 13, wherein said second slice image is immediately adjacent to said first slice in said notional stack, and wherein said CAD proximity marker is shaped conformally to a shape of said CAD detection marker.

15. The system of claim 14, further comprising a processing unit coupled to said user input unit and said display unit, said processing unit being configured to compute at least one user depthwise navigation rate associated with said user navigation commands, said processing unit being further configured to cause said display unit to size said CAD proximity marker at least partially according to said depthwise navigation rate such that said CAD proximity marker appears larger when the user depthwise navigation rate is faster and such that said CAD proximity marker appears smaller when the user depthwise navigation rate is slower.

16. The system of claim 14, said notional stack including a plurality of said slice images in an immediate vertical neighborhood of said first slice image, said neighborhood slice images not containing suspected abnormalities with respect to said identified coordinate location, wherein said display unit displays on each of said neighborhood slice images a corresponding CAD proximity marker at said identified coordinate location, and wherein, for all said neighborhood slice images on one of an upper or lower side of said first slice image in said notional stack, said CAD proximity markers are noticeably chirped between a largest size farthest from the first slice image to a smallest size closest to said first slice image, and wherein said smallest-sized CAD proximity marker is of noticeably larger size than said CAD detection marker.

17. A computer program product embodied in a computer readable storage device containing instructions to a tomosynthesis processing and display system to:
receive first information describing an M-member array of two-dimensional tomosynthesis reconstructed images $Tr_i(x,y)$, $\{i=1, \ldots, M\}$, representative of slices of a breast volume;
receive second information identifying among said M-member array an $L^{th}$ image $Tr_L(x,y)$ therein as requiring display of a computer-aided detection (CAD) detection marker thereon at an identified location $(x_A,y_A)$, said second information further indicating that no images within an N-member adjacent neighborhood $T_k(x,y)$, $\{k=L-N, \ldots, L-1\}$, $N>1$, of $Tr_L(x,y)$ in said M-member array require CAD detection markers near the location $(x_A,y_A)$;
interactively display the images $Tr_i(x,y)$ to a user, wherein the user pages as desired through the images $Tr_i(x,y)$, $\{i=1$ to $M\}$;
when displaying $Tr_L(x,y)$, displaying thereon the CAD detection marker at the identified location $(x_A,y_A)$;
when displaying any of $T_k(x,y)$, $\{k=L-N, \ldots, L-1\}$, displaying thereon a corresponding CAD proximity marker at the identified location $(x_A,y_A)$, wherein each of said N CAD proximity markers is of noticeably different size than said CAD detection marker;
whereby said N CAD proximity markers, while not indicative of detections on their respective images $T_k(x,y)$, $\{k=L-N, \ldots, L-1\}$, encourage user attention toward the identified coordinate location $(x_A,y_A)$ of the $Tr_L(x,y)$ to discourage user oversight of the CAD detection marker thereon when paging therethrough.

18. The computer program product of claim 17, wherein said N CAD proximity markers are chirped in size between a largest size for image $T_{L-N}(X,Y)$ to a smallest size for image $T_{L-1}(X,Y)$.

19. The computer program product of claim 18, wherein each of said N CAD proximity markers is shaped conformally to a shape of said CAD detection marker.

20. The computer program product of claim 17, further containing instructions to the tomosynthesis processing and display system to:

compute at least one user paging rate associated with said interactive display; and vary the size of each of said N CAD proximity markers according to said user paging rate to be larger when said user paging rate is faster and smaller when said user paging rate is slower.

\* \* \* \* \*